US009168020B2

(12) United States Patent
Jain et al.

(10) Patent No.: US 9,168,020 B2
(45) Date of Patent: Oct. 27, 2015

(54) FREQUENCY DOMAIN ANALYSIS TRANSFORM OF RENAL BLOOD FLOW DOPPLER SIGNAL TO DETERMINE STRESS LEVELS

(75) Inventors: Jawahar Jain, Los Altos, CA (US); David L. Marvit, San Francisco, CA (US); Madan Bahadur, Mumbai (IN); Shreyans Gandhi, Mumbai (IN)

(73) Assignee: FUJITSU LIMITED, Kawasaki (JP)

(*) Notice: Subject to any disclaimer, the term of this patent is extended or adjusted under 35 U.S.C. 154(b) by 227 days.

(21) Appl. No.: 13/584,499

(22) Filed: Aug. 13, 2012

(65) Prior Publication Data

US 2014/0046189 A1    Feb. 13, 2014

(51) Int. Cl.
*A61B 8/00* (2006.01)
*A61B 8/06* (2006.01)
*A61B 8/08* (2006.01)

(52) U.S. Cl.
CPC ............. *A61B 8/06* (2013.01); *A61B 8/5223* (2013.01); *A61B 8/488* (2013.01)

(58) Field of Classification Search
CPC .......... A61B 8/06; A61B 8/5223; A61B 8/488
See application file for complete search history.

(56) References Cited

U.S. PATENT DOCUMENTS 5,935,074 A * 8/1999 Mo et al. ................ 600/454
8,529,447 B2 * 9/2013 Jain et al. ............... 600/300

OTHER PUBLICATIONS

Hayashi et al. Vasoconstriction and blood flow responses in visceral arteries to mental task in humans. Experimental Physiology. 91(1):21-220. Oct. 2005.*
Loo et al. Genetic-Optimized Classifer Ensemble for Cortisol Salivary Measurement Mapping to Electrocardiogram Features for Stress Evaluation. PRICAI 2012. pp. 274-284.*
Welch, "Kidney Function", Encyclopedia of Stress, 2007, vol. 2, pp. 557-562.

* cited by examiner

*Primary Examiner* — Jonathan Cwern
(74) *Attorney, Agent, or Firm* — Maschoff Brennan

(57) ABSTRACT

A method of determining stress based on renal blood flow. The method includes receiving data indicating renal blood flow of a subject. The method also includes calculating a power spectrum of a signal derived from the data. The power spectrum indicates a stress level of the subject.

19 Claims, 5 Drawing Sheets

FREQUENCY DOMAIN ANALYSIS TRANSFORM OF RENAL BLOOD FLOW DOPPLER SIGNAL TO DETERMINE STRESS LEVELS

FIELD

The embodiments discussed herein are related to determining stress based on renal blood flow measurements.

BACKGROUND

Mental stress has been defined as "a real or perceived challenge, either endogenous or exogenous, that perturbs body equilibrium or 'homeostasis.' . . . . Whether the person can adapt to or cope with the stress will depend on the nature and severity of the stressor and the person's physical and mental state, which in turn depends on genetic, experiential, social, and environmental factors." See Welch, W. J., *Kidney Function* in Encyclopedia of Stress, 2007, Vol. 2.

Currently there is no reliable method to measure a person's mental stress. One common method that attempts to measure a person's stress is a psychological questionnaire. Some psychological questionnaires are relatively lengthy, requiring a half hour or more to complete. Thus, it is difficult to obtain real-time stress measurements based on questionnaires. Additionally, the filling out of the questionnaire by the person may create stress for the person. Given the time involved in completing the questionnaire and the potential to induce stress in the person, the results obtained by the questionnaire method may be delayed and/or may differ from actual stress which the person normally experiences.

Another method for measuring stress measures stress hormone levels in the blood, urine, or saliva of a person. Such stress hormone levels may become elevated when the person interprets a situation as being stressful. However, the measurement of stress hormones is invasive as it may require a blood, urine, or saliva sample of the person and additionally may be difficult or impossible to use for continuous monitoring.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method of determining stress based on renal blood flow is described. The method includes receiving data indicating renal blood flow of a subject. The method also includes calculating a power spectrum of a signal derived from the data. The power spectrum indicates a stress level of the subject.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
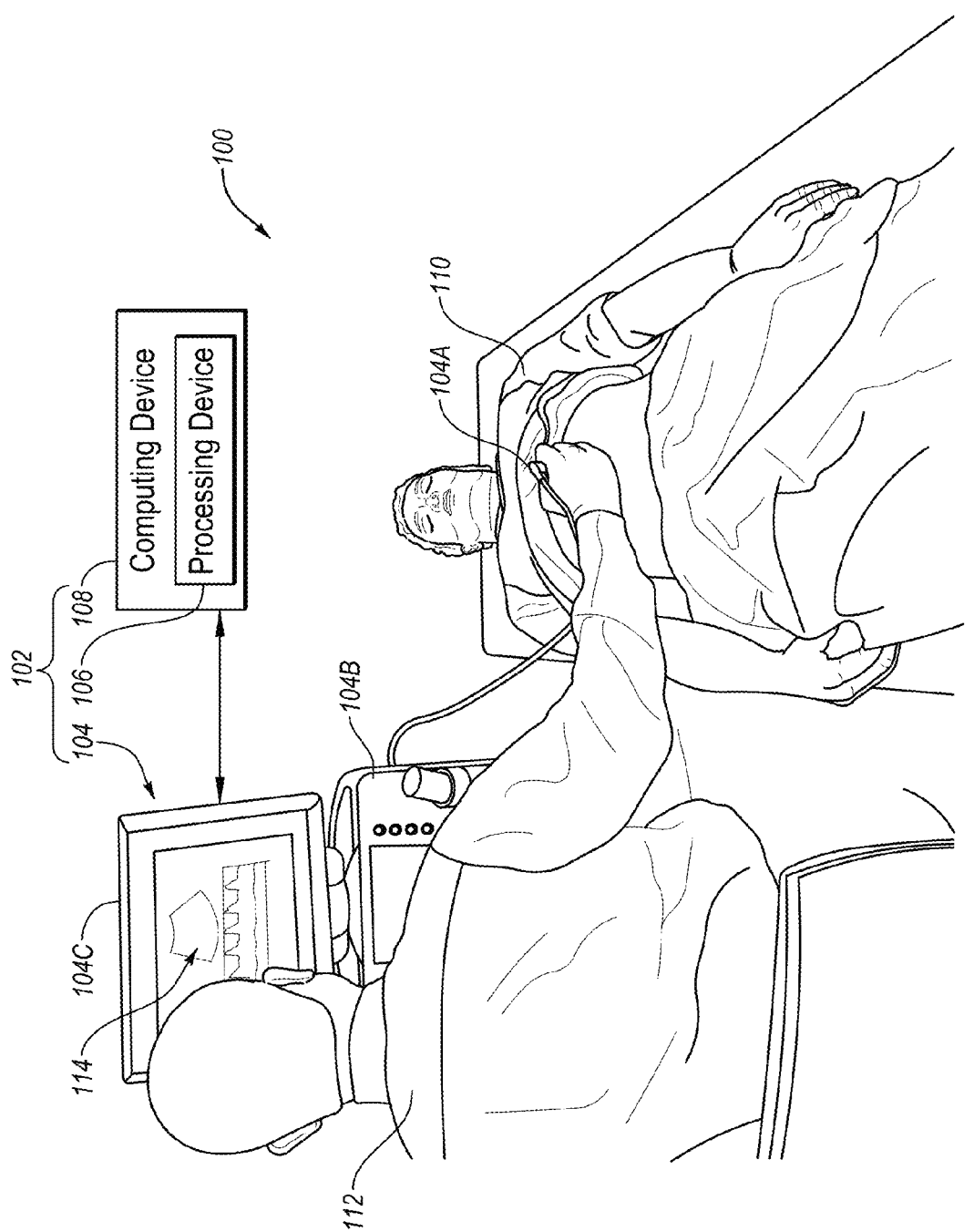
FIG. 1 illustrates an example operating environment in which embodiments of a system of determining stress based on renal blood flow may be implemented.

Every person has an active sympathetic nervous system (SNS), which is responsible for inducing stress, and an active parasympathetic nervous system (PSNS), which is responsible for inducing relaxation. When a person is not stressed, the SNS and PSNS are in a healthy balance, which may be referred to as a baseline period. A person is considered stressed from a medical standpoint when stress hormones are being released over and above what is normal. The stress hormones are released from sympathetic nerves and adrenal glands and may include epinephrine, norepinephrine, and Cortisol, for example. When a person goes through stress, the sympathetic nerves and adrenal glands release such stress hormones.

Cortisol is produced by the adrenal gland in the zona fasciculata, the second of three layers comprising the outer adrenal cortex of the brain. Release of Cortisol is controlled by the hypothalamus, another part of the brain. The secretion of corticotropin-releasing hormone (CRH) by the hypothalamus triggers anterior pituitary secretion of adrenocorticotropic hormone (ACTH). ACTH is carried by the blood to the adrenal cortex, where it triggers glucocorticoid secretion. Its main functions in the body include increasing blood sugar through gluconeogenesis; suppressing the immune system; and aiding in fat, protein, and carbohydrate metabolism. CRH, ACTH and Cortisol are part of the limbic-hypothalamic-pituitary-adrenal (LHPA) axis and are relatively difficult to measure continuously and in real-time.

On the other hand, hormones such as epinephrine and norepinephrine are part of the sympathetic-adrenal-medullary (SAM) axis and may have a relatively immediate effect on various more measurable parameters. In particular, kidneys are rich in sympathetic nerves. When they release stress hormones such as norepinephrine, it then causes renal arteries to constrict. Constriction causes changes in blood flow. Some embodiments described herein detect stressed states generally based on changes in the blood flow through the renal arteries or through a single one of the renal arteries.

Accordingly, an example system of determining stress may include an ultrasound machine, such as a Doppler ultrasound machine, that may be configured to monitor renal blood flow through a renal artery of a subject. The ultrasound machine may generate a velocity waveform of the renal blood flow that fluctuates in a generally periodic fashion with each heartbeat. A computer may be used to calculate a power spectrum of the velocity waveform by, in some embodiments, performing a Fast Fourier Transform (FFT) on the velocity waveform. The power spectrum may indicate a stress level of the subject. The determination of stress by calculating a power spectrum of a velocity waveform of renal blood flow as described in more detail below may generally be referred to herein as the "power spectrum method".

Such power spectra may be obtained at various times. For example, a baseline power spectrum indicating a baseline stress level may be obtained when the subject is in a non-stressed state. Subsequently, a current power spectrum indicating a current stress level of the subject may be obtained and compared to the baseline power spectrum to determine a relative stress level of the subject. When the relative stress level is sufficiently elevated compared to the baseline stress level, a stress-reduction treatment may be recommended, e.g., by a medical physician, for the subject to reduce the relative stress level. The stress reduction treatment may include, for example, a medication, counseling, meditation, or postponement of an imminent medical procedure.

Embodiments of the present invention will be explained with reference to the accompanying drawings.

FIG. 1 illustrates an example operating environment 100 in which embodiments of a system 102 of determining stress based on renal blood flow may be implemented. The system 102 may include an ultrasound machine 104 and a processing device 106. The processing device 106 may be provided separately from the ultrasound machine 104, for example, as part of a separate computing device 108 as illustrated in FIG. 1. Alternately, the processing device 106 may be included in the ultrasound machine 104 such that the computing device 108 may be omitted from the system 102.

As illustrated in FIG. 1, the operating environment 100 further includes a subject 110 and an ultrasound machine operator 112 (hereinafter "operator 112"). The subject 110 may generally include any living being with a renal artery. The subject 110 is illustrated in FIG. 1 as a person such that the system 102 may be used to determine stress of the person based on the person's renal blood flow. However, embodiments described herein may optionally be applied to pet animals, farm animals, research animals, or virtually any animal including a renal artery to determine stress of the animal based on renal blood flow of the animal.

The operator 112 may generally include any individual with the knowledge and ability to correctly operate the ultrasound machine 104 to generate data indicating renal blood flow of the subject 110. Thus, depending on any other training and experience of the operator 112, the operator 112 may include a healthcare worker such as an ultrasound technician, a nurse, a radiologist or other medical physician, or a physician's assistant, or a veterinarian or other non-healthcare worker.

The ultrasound machine 104 may include a Doppler ultrasound machine. Generally, the ultrasound machine 104 may be configured to generate data indicating renal blood flow of the subject 110. In these and other embodiments, the ultrasound machine 104 may include a sonography head 104A, a base unit 104B, and a display device 104C. The sonography head 104A may generally include a piezoelectric transducer encased in a housing. Electrical pulses may be generated by the base unit 104B and provided to the sonography head 104A, causing the piezoelectric transducer of the sonography head 104A to ring, e.g., generate sound waves, at a desired frequency. The desired frequency may be between about two megahertz (MHz) and about eighteen MHz in some embodiments. The sonography head 104A may be configured to focus each generated sound wave so as to come into focus at a desired depth within the body of the subject 110.

Each sound wave may be partially reflected from layers between different tissues within the body of the subject 110. In particular, each sound wave may be at least partially reflected anywhere there are density changes in a path of travel of the sound wave within the body of the subject 110. For example, a density change may occur as each sound wave arrives at a renal artery of the subject 110 and encounters blood flowing through the renal artery, causing at least partial reflection of the sound wave and generating echoes. Some of the echoes return to the piezoelectric transducer of the sonography head 104A and are converted by the piezoelectric transducer to electrical pulses that are returned to the base unit 104B. Thus, the sonography head 104A generates ultrasound data including the electrical pulses and provides it to the base unit 104B.

The base unit 104B may determine, for each echo, a roundtrip time of the echo, e.g., the time from when the corresponding sound wave was first transmitted to when the echo was first received. From the roundtrip time, the base unit 104B may determine the focal length of the sonography head 104A. The base unit 104B may additionally determine a strength of each echo and a frequency shift or Doppler shift of each echo in the case of the sound wave reflecting off of a moving object, such as the blood flowing through the renal artery. From this information, the base unit 104B may generate data indicating renal blood flow of the subject 110, such as a velocity waveform of the renal blood flow. The generated data may include, for example, an image 114 of the velocity waveform of the renal blood flow that may be displayed on the display device 104C, or a data signal representing the velocity waveform of the renal blood flow, or the like.

The processing device 106 may be communicatively coupled to the ultrasound machine 104 such that the processing device 106 may exchange data with, e.g., transmit data to and/or receive data from, the ultrasound machine 104. Thus, whether the processing device 106 is integrated into the ultrasound machine 104 or provided in the separate computing device 108, the processing device 106 may be configured to receive from the ultrasound machine 104 the data indicating renal blood flow of the subject 110 that is generated by the ultrasound machine 104.

The processing device 106 may be further configured to calculate a power spectrum of a signal derived from the data, the power spectrum indicating a stress level of the subject 110. When the data includes the image 114 of the velocity waveform of the renal blood flow of the subject 110 or data representing the image 114, the signal derived from the data may include extracted data points representing an envelope of the velocity waveform, the extracted data points collectively forming the signal. When the data includes a data signal representing the velocity waveform of the renal blood flow, the signal derived from the data may include the data signal.

The power spectrum may be calculated by the processing device 106 by performing an FFT on the signal derived from the data generated by the ultrasound machine 104 to generate the power spectrum of the signal as a function of frequency. The power spectrum may be displayed on the display device 104C of the ultrasound machine 104, on a display device included in or attached to the computing device 108, or the like. Alternately or additionally, multiple power spectra may be simultaneously displayed on any of the foregoing display devices for comparison.

In some embodiments, a baseline power spectrum may be obtained from data generated by the ultrasound machine 104 as described above during a period of time when the subject 110 is not stressed to be used subsequently for reference. Such data may be referred to as baseline data. Subsequently, and prior to a medical procedure such as a surgery or at some other time when the subject 110 is likely to be experiencing stress, the ultrasound machine 104 may be used to obtain current data indicating renal blood flow of the subject 110 at a current time. The processing device 106 may receive the current data and may calculate a current power spectrum of a signal derived from the current data, the current power spectrum indicating a current stress level of the subject 110. The current power spectrum may be compared to the baseline power spectrum to determine a relative stress level of the subject 110. The relative stress level may correspond to a difference between the current stress level and the baseline stress level, for example.

When the current stress level and/or the relative stress level is above a predetermined threshold, a stress-reduction treatment may be recommended for the subject 110 to reduce the relative stress level. The stress-reduction treatment may include a medication, counseling, meditation, postponement of an imminent medical procedure, or any other suitable treatment for reducing stress. There is a correlation between medical procedure outcomes and stress, including for medical procedures such as surgeries. Accordingly, the stress-reduction treatment may be recommended for the subject 110 to improve the likelihood of a successful outcome of an imminent medical procedure for the subject 110. Alternately or additionally, the stress-reduction treatment may be recommended to improve the overall health of the subject 110 or for some other reason.

Moreover, the stress-reduction treatment may be recommended by a nurse, medical physician, physician's assistant, or the like, which may include the operator 112 in some embodiments. Alternately or additionally, the processing device 106 may be configured to generate the recommendation based at least on the current stress level and/or the relative stress level, among potentially other information such as a digital medical history of the subject 110 accessible to the processing device 106.

Some embodiments disclosed herein alternately or additionally include displaying stress information on the ultrasound machine 104, or more particularly on the display device 104C of the ultrasound machine 104. The stress information may include a stress level or relative stress level or the like of the subject. The stress information may be determined according to the power spectrum method, according to the Doppler RI method described in more detail below, or more generally according to any suitable method.

Figure 2A:
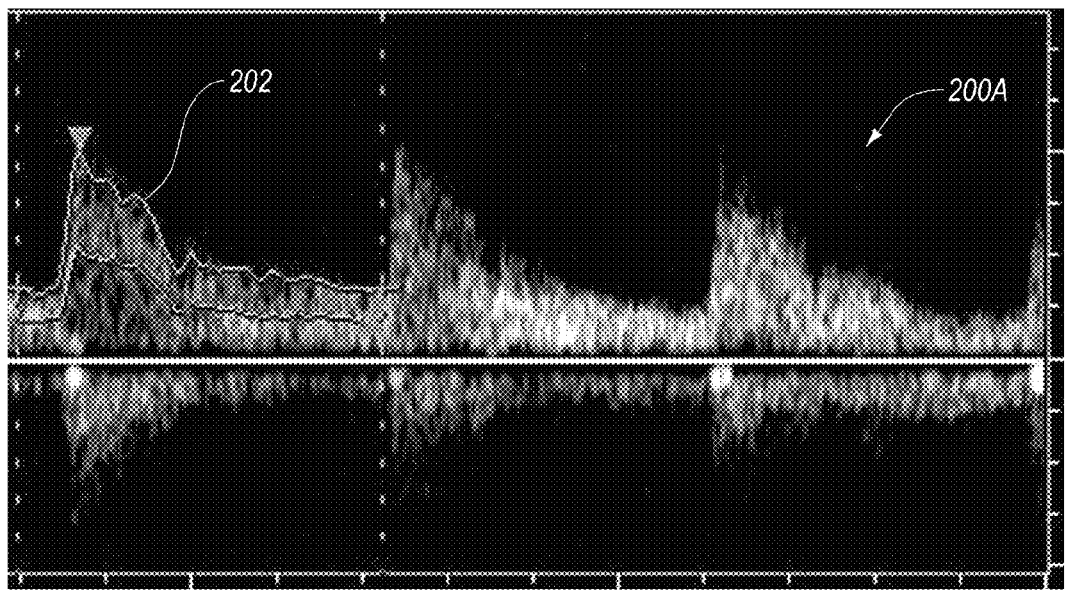
FIGS. 2A-2B illustrate a first velocity waveform and a second velocity waveform such as may be generated by an ultrasound machine included in the system of FIG. 1.
Figure 2B:
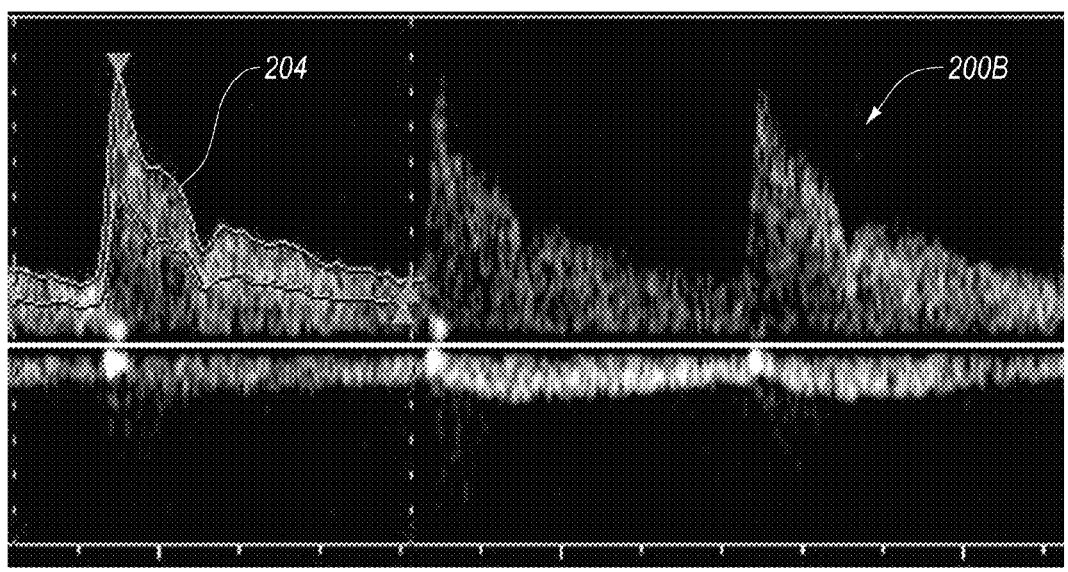

FIGS. 2A-2B illustrate a first velocity waveform 200A (hereinafter "first waveform 200A") and a second velocity waveform 200B (hereinafter "second waveform 200B") such as may be generated by the ultrasound machine 104 of FIG. 1. The vertical axis in each of FIGS. 2A-2B corresponds to velocity, e.g., of the blood flowing through the renal artery, while the horizontal axis in each of FIGS. 2A-2B corresponds to time.

In general, an ultrasound machine, such as the ultrasound machine 104, may be operated to generate first data indicating renal blood flow of a subject, such as the subject 110, during a period of time when the subject is not stressed (hereinafter referred to as a non-stressed state), which first data may be graphically illustrated as the first waveform 200A of FIG. 2A. In addition, the ultrasound machine may be operated to generate second data indicating renal blood flow of the same subject during a different period of time when the subject is experiencing stress (hereinafter referred to as a stressed stated), which second data may be graphically illustrated as the second waveform 200B of FIG. 2B.

As seen in FIGS. 2A-2B, each of the first and second waveforms 200A, 200B fluctuates in a generally periodic fashion corresponding to heartbeat cycles. Particularly, there are three peaks in each of the first and second waveforms 200A, 200B, each of the peaks generally corresponding to a point in a corresponding heartbeat cycle where blood pressure is at its highest for the heartbeat cycle. The value (along the vertical axis) of each peak is the peak systolic velocity of renal blood flow for the corresponding heartbeat cycle. There are also four troughs in each of the first and second waveforms 200A, 200B, each of the troughs generally corresponding to a point in the corresponding heartbeat cycle where blood pressure is at its lowest for the heartbeat cycle. The value (along the vertical axis) of each trough is the peak diastolic velocity of renal blood flow for the corresponding heartbeat cycle. Thus, at the peaks when the blood pressure in the corresponding heartbeat cycle is at its highest, blood flow through the renal artery is also generally at its highest, while at the troughs when the blood pressure in the corresponding heartbeat cycle is at its lowest, blood flow through the renal artery is also generally at its lowest, as illustrated in FIGS. 2A-2B.

It may generally be seen from a visual comparison of the first waveform 200A and the second waveform 200B that the second waveform 200B corresponding to the stressed state of the subject is different than the first waveform 200A corresponding to the non-stressed state of the subject. For example, the second waveform 200B appears to have higher peaks than the first waveform 200A, and the second waveform 200B also appears to have a somewhat different upper envelope than the first waveform 200A.

One method of determining stress calculates a Resistive Index (RI) of the renal artery based on waveforms such as those depicted in FIGS. 2A-2B. In particular, the RI may be calculated from a value of a given peak and a value of a corresponding trough, and more particularly, according to the formula $RI=(S-D)/S$ where S is the peak systolic velocity and D is the peak diastolic velocity.

Various RI measurements for eight different subjects calculated from velocity waveforms such as those illustrated in FIGS. 2A-2B and obtained during four different times for each of the eight subjects are included in Table 1 below.

TABLE 1

| Subject No. | Baseline RI | Stress1 RI | Stress2 RI | Relaxation RI |
|---|---|---|---|---|
| 1 | 0.62 | 0.72 | 0.79 | 0.61 |
| 2 | 0.56 | 0.69 | 0.72 | 0.57 |
| 3 | 0.62 | 0.72 | 0.71 | 0.54 |
| 4 | 0.3 | 0.78 | 0.78 | 0.62 |
| 5 | 0.60 | 0.74 | 0.73 | 0.47 |
| 6 | 0.62 | 0.85 | 0.88 | 0.54 |
| 7 | 0.65 | 0.79 | 0.73 | 0.62 |
| 8 | 0.64 | 0.76 | 0.74 | 0.64 |

A baseline RI ("Baseline RI") for each of the subjects was calculated from a velocity waveform obtained when the subject was in a non-stressed state. A first stress event RI ("Stress1 RI") for each of the subjects was calculated from a velocity waveform obtained when the subject was in a first stress state. In the present example, the first stress state was induced by the administration of an examination of the corresponding subject by a medical physician. A second stress event RI ("Stress2 RI") for each of the subjects was calculated from a velocity waveform obtained when the subject was in a second stress state. In the present example, the second stress state was induced by indicating to each subject that a blood sample was needed by application of a pinprick, but the pinprick was never actually applied. A relaxation RI ("Relaxation RI") for each of the subjects was calculated from a velocity waveform obtained after the subject had been subjected to a relaxation therapy.

It may be seen from Table 1 that the RI of the renal artery increases with an increase in stress and decreases with a decrease in stress. Indeed, determining stress by obtaining a velocity waveform of renal blood flow followed by calculating the RI of the renal artery (referred to hereinafter as the "Doppler RI method") is a relatively accurate method of determining the stress level of a subject that may be implemented to determine stress levels substantially in real-time. However, the Doppler RI method is somewhat intolerant to noise because even a single jitter in the corresponding renal blood flow velocity waveform with an amplitude greater than the actual peak systolic velocity can be erroneously identified as the peak systolic velocity, leading to an erroneous calculation of the RI.

There are numerous potential sources of noise when obtaining velocity waveforms of renal blood flow. For instance, movement of the corresponding sonography head, movement of the subject, and/or movement of gastric gases within the subject may introduce noise in the corresponding sonographic measurements. Noise may nevertheless be substantially eliminated and/or reduced in this and other embodiments by manually or automatically pruning noisy portions of each velocity waveform therefrom. In particular, given the periodic nature of the velocity waveforms for renal blood flow, sequential repeating portions of each velocity waveform may generally be similar in width, height and form. Thus, sequential portions of a given velocity waveform that are not similar in width, height and form may be pruned, or discarded, from the velocity waveform. The pruning may be performed by an operator of the corresponding ultrasound machine during acquisition of the velocity waveform, or at any time on a pre-recorded velocity waveform.

Some embodiments described herein improve a noise resilience of stress level calculations based on renal blood flow compared to the Doppler RI method by calculating a power spectrum of the velocity waveform. In particular, the noise resilience may be improved compared to the Doppler RI method because jitter/noise generally contributes to higher frequency spectrum components of the renal blood flow velocity waveform, whereas the power spectrum method according to some embodiments relies on relatively lower frequency spectrum components of the renal blood flow velocity waveform.

As previously indicated, the actual data used for the power spectrum calculation may depend on the data received by a corresponding processing device, such as the processing device 106, from a corresponding ultrasound machine, such as the ultrasound machine 104. With continued reference to FIGS. 2A-2B, in an example embodiment, the data received at the processing device may include an image of the first or second waveform 200A, 200B, for example. In this and other embodiments, the processing device may extract data points representing the envelope of the first or second waveform 200A, 200B from the corresponding image. The extracted data points may collectively form a signal 202 or 204 from which the power spectrum of the corresponding first or second waveform 200A, 200B may be calculated.

Alternately or additionally, the data generated by the ultrasound machine and received by the processing device may include a data signal substantially identical to the signal 202 or 204. Accordingly, the processing device may calculate the power spectrum using the data signal received from the ultrasound machine (or other source such as a computer storage medium) without first extracting data points from an image received from the ultrasound machine.

Figure 3:
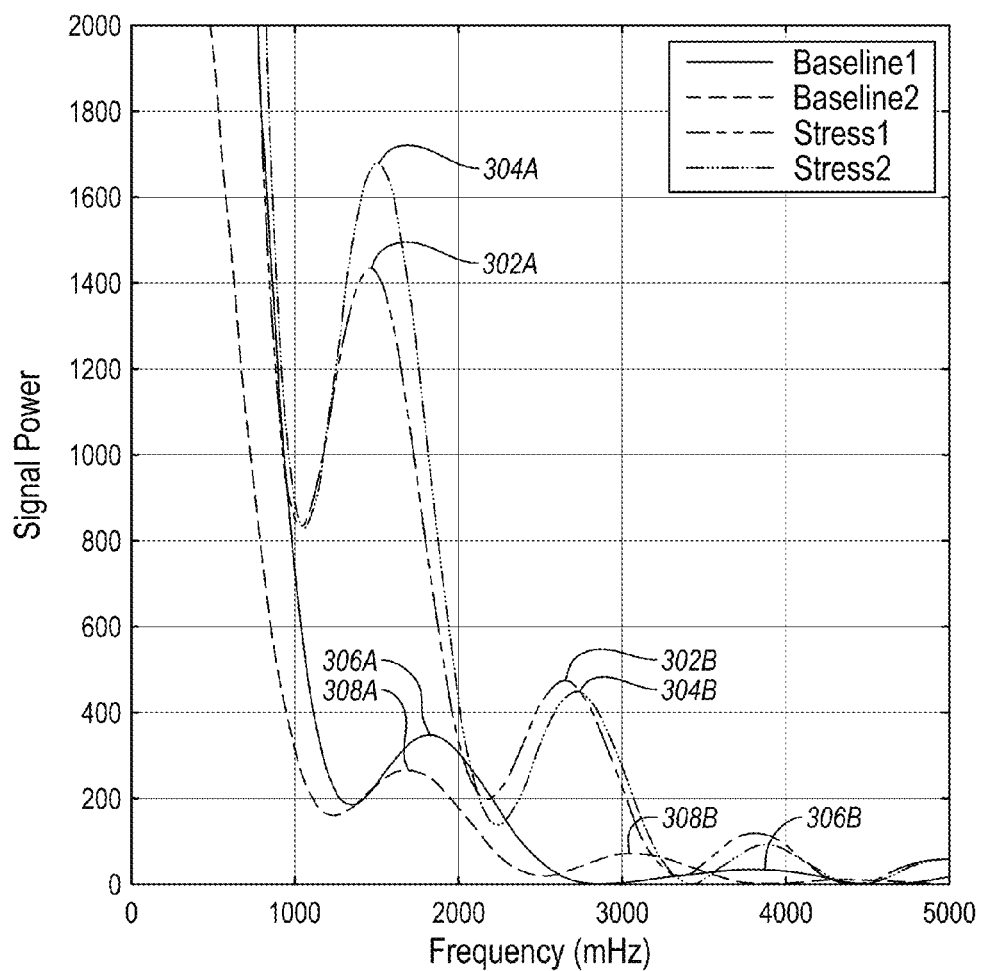
FIG. 3 illustrates various power spectra that may be calculated from corresponding velocity waveforms of renal blood flow of a subject.

FIG. 3 illustrates various power spectra that may be calculated from corresponding velocity waveforms of renal blood flow of a subject, such as the first and second waveforms 200A, 200B of FIGS. 2A-2B, or from signals derived from other data indicating renal blood flow of a subject. More particularly, the power spectra illustrated in FIG. 3 include a first baseline (hereinafter "baseline1") power spectrum, a second baseline (hereinafter "baseline2") power spectrum, a first stress event (hereinafter "stress1") power spectrum, and a second stress event (hereinafter "stress2") power spectrum.

All of the power spectra of FIG. 3 correspond to a single subject. Additionally, all of the power spectra of FIG. 3 were calculated by performing an FFT of a corresponding velocity waveform of renal blood flow. More generally, power spectra and/or stress measurements according to embodiments described herein may be calculated from corresponding velocity waveforms of renal blood flow by performing any suitable signal analysis technique on the velocity waveform. Examples of suitable signal analysis techniques include, but are not limited to, FFTs, curve shape analysis and shape approximations. In the shape approximation technique, for instance, the velocity waveform for a particular heart beat cycle may be generalized as a triangle or other shape, and then the peak, slope of one or more sides, and/or the area of the triangle or other shape may be determined and compared against the peak, slope of one or more sides, and/or area of a triangle or other shape generalized from a velocity waveform obtained at some other time.

In the example of FIG. 3, the baseline1 power spectrum was calculated from a velocity waveform obtained when the subject was in a first non-stressed state. The baseline2 power spectrum was calculated from a velocity waveform obtained when the subject was in a second non-stressed state. The stress1 power spectrum was calculated from a velocity waveform obtained when the subject was in a first stress state. The stress2 power spectrum was calculated from a velocity waveform obtained when the subject was in a second stress state.

As illustrated in FIG. 3, each of the stress1 and stress2 power spectra are visibly different from the baseline1 and baseline2 power spectra. For instance, each of the stress1 and stress2 power spectra include a first peak 302A or 304A at about 1500 millihertz (mHz) and a second peak 302B or 304B at about 2700 mHz, whereas each of the baseline1 and baseline2 power spectra include a first peak 310, 312 at about 1700 mHz and a second peak 314, 316 at greater than 3000 mHz.

Additionally, the first peaks 302A, 304A of both of the stress1 and stress2 power spectra are significantly higher than either of the first peaks 306A, 308A of the baseline1 and baseline2 power spectra. In some embodiments, a relative stress level of the subject in either of the first or second stress state may be calculated as a difference between the amplitude (e.g., the value on the vertical axis) of the first peak 302A or 302B of the stress1 or stress2 power spectrum and amplitude of the first peak 306A, 306B of a given one of the baseline1 or baseline2 power spectrum.

Although FIG. 3 only illustrates power spectra for a single subject, Applicants have calculated power spectra for all eight of the subjects of Table 1 using the same velocity waveforms from which the RI calculations of Table 1 were derived. Table 2 includes amplitudes of the first peak in (1) each of the power spectra corresponding to the velocity waveform of the non-stressed state corresponding to the Baseline RI of Table 1 (identified in Table 2 as "Baseline Amplitude"), (2) each of the power spectra corresponding to the velocity waveform of the first stress state corresponding to the Stress1 RI of Table 1 (identified in Table 2 as "Stress1 Amplitude"), and (3) each of the power spectra corresponding to the velocity waveform of the second stress state corresponding to the Stress2 RI of Table 1 (identified in Table 2 as "Stress2 Amplitude").

TABLE 22

| Subject No. | Baseline Amplitude | Stress1 Amplitude | Stress2 Amplitude |
|---|---|---|---|
| 1 | 0267 | 1434 | 1678 |
| 2 | 0674 | 1267 | 1400 |
| 3 | 0423 | 0673 | 0673 |
| 4 | 0866 | 1387 | 1386 |
| 5 | 1580 | 3435 | 3091 |
| 6 | 0670 | 4226 | 3337 |
| 7 | 1556 | 3766 | 3806 |
| 8 | 1564 | 4574 | 5412 |

It is evident from Table 2 that different subjects have different baseline and stress state first peak amplitudes, but the baseline and stress state may nevertheless be clearly identified from the change in peak amplitudes. Thus, Table 2 suggests that every person has a different baseline stress level and a common or universal method to detect stress may be incapable of detecting stress if individual differences are not taken into account.

It may be seen from Tables 1 and 2 that changes from a non-stressed state to stressed states based on changes in first peak amplitude of calculated power spectra, e.g., according to the power spectrum method, as described herein may be significantly amplified compared to changes from the non-stressed state to stressed states based on changes in RI calculated according to the Doppler RI method. For example, Table 3 includes, for the eight subjects of Tables 1 and 2, the percent change in stress calculated using both the Doppler RI method and the power spectrum method from the non-stressed state corresponding to the Baseline RI of Table 1 to the first stress state corresponding to the Stress1 RI (identified in Table 3 as "Baseline to Stress 1") and from the non-stressed state corresponding to the Baseline RI of Table 1 to the second stress state corresponding to the Stress2 RI (identified in Table 3 as "Baseline to Stress 2"). The percent change according to the Doppler RI method is identified in Table 3 as "RI (%)" and the percent change according to the power spectrum method is identified in Table 3 as "Amp (%)" (corresponding to the percent change in first peak amplitude).

TABLE 3

| Subject No. | Baseline to Stress 1 | | Baseline to Stress 2 | |
|---|---|---|---|---|
| | RI (%) | Amp (%) | RI (%) | Amp (%) |
| 1 | 16.12 | 437.07 | 27.41 | 528.46 |
| 2 | 23.21 | 87.98 | 28.57 | 107.71 |
| 3 | 16.12 | 59.10 | 14.51 | 59.10 |
| 4 | 23.80 | 60.16 | 23.80 | 60.04 |
| 5 | 23.33 | 117.40 | 21.66 | 95.63 |
| 6 | 37.09 | 530.74 | 41.93 | 598.05 |
| 7 | 21.53 | 142.03 | 12.30 | 144.60 |
| 8 | 18.75 | 192.45 | 15.62 | 246.03 |

It may be seen from Table 3 that the power spectrum method generally agrees with the Doppler RI method insofar as when stress calculated according to the Doppler RI method increases, stress calculated according to the power spectrum method also increases. Further, the percent change in the stress calculation is significantly amplified in the power spectrum method compared to the Doppler RI method.

For example, the average percent change according to the Doppler RI method is about 23% in Table 3. A maximum percent change of 48% calculated according to the Doppler RI method has been reported. See Welch, W. J., *Kidney Function* in Encyclopedia of Stress, 2007, Vol. 2. In comparison, the average percent change according to the power spectrum method is about 217% in Table 3, almost ten times larger than the average percent change according to the Doppler RI method. The significantly larger percent change according to the power spectrum method may be tapped to accurately detect onset of acute stress. The significantly larger percent change according to the power spectrum method also makes the power spectrum method relatively more noise resilient than the Doppler RI method and relatively more sensitive to even small changes in stress levels. The foregoing features of the power spectrum method may not be possible in other stress calculation methods such as the Doppler RI method since small changes in RI of the renal artery may not be considered physiologically meaningful.

Figure 4:
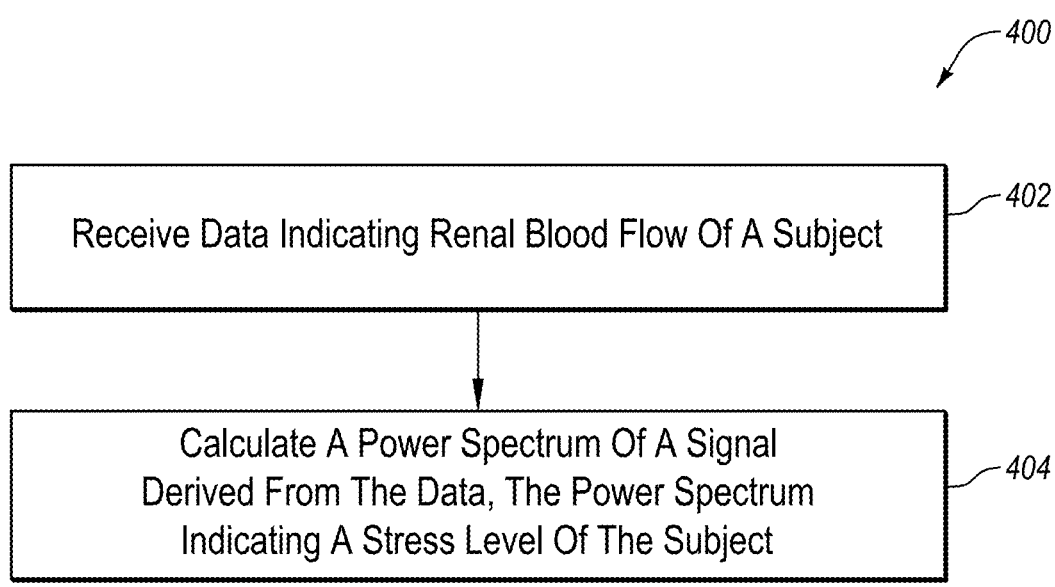
FIG. 4 shows an example flow diagram of a method of determining stress based on renal blood flow.

FIG. 4 shows an example flow diagram of a method 400 of determining stress based on renal blood flow. The method 400 and/or variations thereof may be implemented, in whole or in part, by a system, such as the system 102 of FIG. 1. Alternately or additionally, the method 400 and/or variations thereof may be implemented, in whole or in part, by a processor or other processing device, such as the processing device 106 of FIG. 1. Although illustrated as discrete blocks, various blocks may be divided into additional blocks, combined into fewer blocks, or eliminated, depending on the desired implementation.

The method 400 may begin at block 402 in which data indicating renal blood flow of a subject is received. The data may include or represent a velocity waveform of renal blood flow in a renal artery of the subject. For example, the data may include an image of the velocity waveform of the renal blood flow. Alternately, the data may include a data signal representing the velocity waveform of the renal blood flow.

In block 404, a power spectrum of a signal derived from the data may be calculated. In these and other embodiments, the signal derived from the data may include data points representing an envelope of the velocity waveform that are extracted from an image of the velocity waveform. Alternately, where the data received in block 402 includes a data signal representing the velocity waveform, the signal derived from the data may include the data signal. Additionally, the power spectrum calculated in block 404 may indicate a stress level of the subject. For example, a value of a first peak, such as the first peak 302A, 304A, 306A, 308A of the power spectra of FIG. 3, may be used as the stress level of the subject. Alternately or additionally, calculating the power spectrum may include performing an FFT on the signal derived from the data to generate the power spectrum of the signal as a function of frequency.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

For example, where the data received in block 402 includes an image of the velocity waveform, the method 400 may additionally include deriving the signal from the data by extracting data points representing the envelope of the velocity waveform from the image, the extracted data points collectively forming the signal.

Optionally, the data received in block 402 may include first data collected when the subject is in a non-stressed state and the power spectrum may include a first power spectrum representing a baseline stress level of the subject. In these and other embodiments, the method may further include assessing a current stress level of the subject by receiving second data indicating renal blood flow of the subject at a current time. A second power spectrum of a signal derived from the second data may be calculated, the second power spectrum indicating the current stress level of the subject. The second power spectrum may be compared to the first power spectrum to determine a relative stress level of the subject corresponding to a difference between the current stress level and the baseline stress level.

The current time may correspond to a time in advance of an imminent medical procedure, such as an imminent surgery, or a time after a completed medical procedure. A stress-reduction treatment may be recommended for the subject to reduce the relative stress level. The stress-reduction treatment may include at least one of a medication, counseling, meditation, or postponement of the imminent medical procedure.

Alternately or additionally, it may be recommended to postpone a medical procedure until a later time. Additionally, a stress reduction treatment may be recommended for the subject to reduce the relative stress level prior to the later time and to improve a likelihood of a successful outcome to the medical procedure. The stress reduction treatment may include a medication, counseling or meditation, for instance.

In some embodiments, the data received in block 402 may include first data as already indicated. Second data including measurements of a biological function of the subject may be received, the second data being captured simultaneously with the first data. The biological function may include cardiac function, respiratory function, adrenal function, or some other biological function. Accordingly, the second data may include measurements of, for example, heart rate, breathing rate, blood Cortisol levels, salivary Cortisol levels, or the like. A stress level of the subject may be calculated based on the second data using a stress algorithm of calculating stress based on measurements of the biological function. Examples of such stress algorithms may include a Cortisol measurement method, an LF/HF stress marker method, or a pNN stress marker method, all of which are briefly described below. The stress algorithm may then be tuned so that the stress level calculated according to the stress algorithm corresponds to the stress level indicated by the power spectrum. For example, the stress algorithm may be tuned so as to agree with the power spectrum model. In particular, the stress algorithm may be tuned so that when the power spectrum indicates an elevated stress level compared to a baseline stress level, the stress level calculated according to the stress algorithm also indicates an elevated stress level.

As previously indicated, a subject may be stressed from a medical standpoint when stress hormones such as Cortisol are released above and beyond what is normal. Thus, one stress algorithm referred to herein as the Cortisol measurement method may measure Cortisol levels in the blood, saliva or urine to determine a stress level of the subject. However, Cortisol levels change slowly with acute stress and have marked circadian variations. Thus, determinations of stress levels based solely on Cortisol measurements may be inaccurate and may be tuned by taking into account one or more other parameters, such as heart rate, breathing rate, or the like.

The stress algorithms referred to herein as the LF/HF stress marker method involves analysis of heart rate variability (HRV) of a subject. The HRV analysis may be carried out in the frequency domain or the time domain. In the frequency domain analysis, a frequency transform of a heart rate waveform of the subject is taken and frequency bands are defined for very low frequency (VLF) regions, low frequency (LF) regions and high frequency (HF) regions. The power of the spectrum in these regions may depend on stress such that a LF/HF power ratio may be taken as a stress level of the subject. In the time domain analysis, the heart rate change in subsequent heart beats is basically correlated with the stress. Known LF/HF-based stress algorithms have been determined by Applicants to be inaccurate insofar as LF/HF stress measurements often disagree with Doppler RI stress measurements and by extension power spectrum stress measurements. Thus, the LF/HF stress marker method may be tuned for consistency with the Doppler RI method and/or the power spectrum method as described herein.

The stress algorithms referred to herein as the pNN stress marker method calculate time-domain parameters directly from an RR interval time series. The time-domain parameters may include the mean and standard deviation of the RR intervals. The standard deviation of RR intervals (SDNN) describes the overall variation in the RR interval signal while the standard deviation of the differences between consecutive RR intervals (SDSD) describes short-term variation. For a stationary time series, SDSD is equal to the root mean square (RMS) of the differences between consecutive RR intervals (RMSSD). There are also other commonly used parameters like NNx which is the number of consecutive RR intervals differing more than x miliseconds (ms). The pNNx parameter is the percentage value of NNx intervals. The prefix NN stands for normal-to-normal intervals (i.e., intervals between consecutive QRS complexes resulting from sinus node depolarizations). In practice, RR and NN intervals usually appear to be the same. Known pNN-based stress algorithms have been determined by Applicants to correlate better to the Doppler RI method, and thus to the power spectrum method, than LF/HF-based stress algorithms, although the correlation between the pNN-based stress algorithms and the Doppler RI method is not 100%. Thus, the pNN stress marker method may be tuned for consistency with the Doppler RI method and/or the power spectrum method as described herein.

Embodiments described herein additionally include other stress algorithms that Applicants have determined to have good correlation with the Doppler RI method and/or the power spectrum method. For example, some embodiments described herein include stress algorithms such as the RRIA method and the weighted RRIA method briefly mentioned above.

Figure 5:
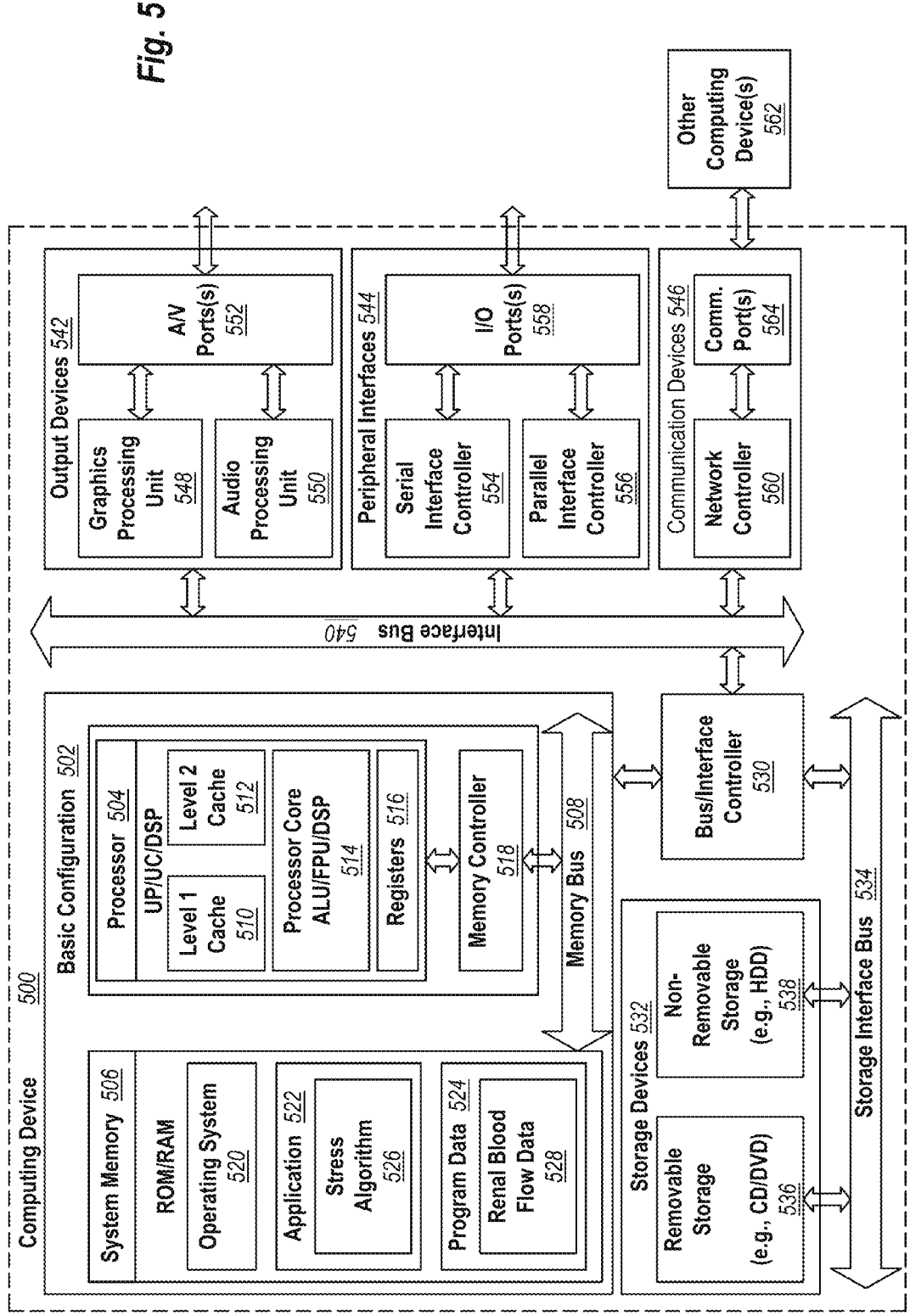
FIG. 5 is a block diagram illustrating an example computing device that is arranged for determining stress based on renal blood flow in accordance with the present disclosure.

FIG. 5 is a block diagram illustrating an example computing device 500 that is arranged for determining stress based on renal blood flow in accordance with the present disclosure. The computing device 500 may correspond to the computing device 108 and/or the base unit 104B of FIG. 1, for example. In a very basic configuration 502, the computing device 500 may include one or more processors 504 and a system memory 506. A memory bus 508 may be used for communicating between the processor 504 and the system memory 506.

Depending on the desired configuration, the processor 504 may be of any type including but not limited to a microprocessor (µP), a microcontroller (µC), a digital signal processor (DSP), or any combination thereof. The processor 504 may include one more levels of caching, such as a level one cache 510 and a level two cache 512, a processor core (or cores) 514, and registers 516. An example processor core 514 may include an arithmetic logic unit (ALU), a floating point unit (FPU), a digital signal processing core (DSP Core), or any combination thereof. An example memory controller 518 may also be used with the processor 504, or in some implementations the memory controller 518 may be an internal part of the processor 504. The processor 504 may be configured to perform one or more of the operations described herein by, for example, executing computer instructions or code loaded into the system memory 506 and/or by executing computer instructions or code line-by-line without using the system memory 506.

Depending on the desired configuration, the system memory 506 may be of any type including but not limited to volatile memory (such as Random Access Memory (RAM)), non-volatile memory (such as Read Only Memory (ROM), flash memory, etc.) or any combination thereof. The system memory 506 may include an operating system 520, one or more applications 522, and program data 524. The application 522 may include a stress algorithm 526 that is arranged to perform one or more of the operations associated with obtaining and processing data indicating renal blood flow of a subject to determine stress of the subject as described herein, including one or more of the operations described with respect to FIG. 4. For example, the application 522 may be executed by the processor 504 to cause the computing device 500 to perform the functions as described herein. The program data 524 may include data 528 indicating renal blood flow of a subject (hereinafter "renal blood flow data 528") such as may be generated by and/or received from an ultrasound machine, such as the ultrasound machine 104 of FIG. 1, as is described herein. In some embodiments, the application 522 may be arranged to operate with the program data 524 on the operating system 520 such that stress of a subject may be determined based on the renal blood flow data 528.

The computing device 500 may have additional features or functionality, and additional interfaces to facilitate communications between the basic configuration 502 and other devices and interfaces. For example, a bus/interface controller 530 may be used to facilitate communications between the basic configuration 502 and one or more data storage devices 532 via a storage interface bus 534. The data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer-readable instructions, data structures, program modules, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (e.g., output devices 542, peripheral interfaces 544, and/or communication devices 546) to the basic configuration 502 via the bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, etc.) or other peripheral devices (e.g., printer, scanner, etc.) via one or more I/O ports 558. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer-readable media as used herein may include both storage media and communication media.

The computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. The computing device 500 may also be implemented as a personal computer including both laptop computer and non-laptop computer configurations.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A method of determining stress based on renal blood flow, the method comprising:
receiving first data indicating a first velocity waveform of renal blood flow of a subject, wherein the first data is collected when the subject is in a non-stressed state and the first data indicating the first velocity waveform of renal blood flow is generated by:
an ultrasound machine emitting sound waves into the subject that encounter blood that flows through a renal artery of the subject;
the ultrasound machine receiving echoes of the emitted sound waves that result from at least partial reflection of the sound waves that encounter the blood that flows through the renal artery of the subject;
the ultrasound machine determining a Doppler shift of each of the echoes; and
based at least on the Doppler shift determined for each of the echoes, the ultrasound machine generating a spectrogram of renal blood flow velocity versus time that includes the first velocity waveform of renal blood flow;
calculating a first power spectrum of first maximum blood flow velocity of the first velocity waveform of renal blood flow, the first power spectrum indicating a baseline stress level of the subject;
assessing a current stress level of the subject by:
receiving second data indicating a second velocity waveform of renal blood flow of the subject at a current time;
calculating a second power spectrum of second maximum blood flow velocity of the second velocity waveform of renal blood flow, the second power spectrum indicating the current stress level of the subject; and
comparing the second power spectrum to the first power spectrum to determine a relative stress level of the subject corresponding to a difference between the current stress level and the baseline stress level; and
in response to the relative stress level exceeding a predetermined threshold, recommending a stress-reduction treatment for the subject to reduce the relative stress level.

2. The method of claim 1, wherein the first data comprises an image of the first velocity waveform of the renal blood flow, the method further comprising deriving the first maximum blood flow velocity from the first data by extracting data points representing an envelope of the first velocity waveform from the image, the extracted data points collectively forming the first maximum blood flow velocity.

3. The method of claim 1, wherein the calculating comprises performing a Fast Fourier Transform (FFT) on the first maximum blood flow velocity to generate the first power spectrum of the first maximum blood flow velocity as a function of frequency.

4. The method of claim 1, wherein the stress-reduction treatment comprises at least one of a medication, counseling, or meditation.

5. The method of claim 1, further comprising, in response to the relative stress level exceeding the predetermined threshold, recommending postponement of a medical procedure until a later time, wherein the stress-reduction treatment is recommended for the subject to reduce the relative stress level prior to the later time and to improve a likelihood of a successful outcome to the medical procedure.

6. The method of claim 1, further comprising:
receiving third data comprising measurements of a biological function of the subject, the third data being captured simultaneously with the first data;
calculating a stress level of the subject based on the third data using a stress algorithm of calculating stress based on measurements of the biological function; and
tuning the stress algorithm so that the stress level calculated according to the stress algorithm corresponds to the stress level indicated by the first power spectrum.

7. The method of claim 1, further comprising outputting the power spectrum or stress information derived from the power spectrum to a display device for analysis of the subject's stress level by a healthcare provider.

8. A system of determining stress based on renal blood flow, the system comprising:
an ultrasound machine configured to generate data indicating a velocity waveform of renal blood flow of a subject by:
emitting sound waves into the subject that encounter blood that flows through a renal artery of the subject;
receiving echoes of the emitted sound waves that result from at least partial reflection of the sound waves that encounter the blood that flows through the renal artery of the subject;
determining a Doppler shift of each of the echoes; and
based at least on the Doppler shift determined for each of the echoes, generating a spectrogram of renal blood flow velocity versus time that includes the velocity waveform of renal blood flow;
a processing device communicatively coupled to the ultrasound machine, the processing device configured to:
receive the data from the ultrasound machine; and
calculate a power spectrum of maximum blood flow velocity of the velocity waveform of renal blood flow, the power spectrum indicating a stress level of the subject; and
a display device coupled to the processing device and configured to display the stress level derived from the power spectrum to a healthcare worker.

9. The system of claim 8, wherein the processing device is configured to calculate the power spectrum of the maximum blood flow velocity by performing a Fast Fourier Transform (FFT) on the maximum blood flow velocity.

10. The system of claim 8, wherein the ultrasound machine comprises a Doppler ultrasound machine.

11. The system of claim 8, wherein the processing device is further configured to output the power spectrum to the display device for display of the power spectrum.

12. The system of claim 11, further comprising a computer readable storage medium coupled to the processing device, wherein:
the calculated power spectrum comprises a current power spectrum representing a current stress level of the subject;
the computer readable storage medium includes baseline data comprising a baseline power spectrum representing a baseline stress level of the subject;
the processing device is further configured to output the baseline power spectrum simultaneously with the current power spectrum for comparison of the current stress level of the subject with the baseline stress level of the subject.

13. A processor configured to execute computer instructions to cause a computing system to perform operations for determining stress based on renal blood flow, the operations comprising:
receiving first data indicating a first velocity waveform of renal blood flow of a subject, wherein the first data is collected during an absence of stress events and the first data indicating the first velocity waveform of renal blood flow is generated by:
an ultrasound machine emitting sound waves into the subject that encounter blood that flows through a renal artery of the subject;
the ultrasound machine receiving echoes of the emitted sound waves that result from at least partial reflection of the sound waves that encounter the blood that flows through the renal artery of the subject;
the ultrasound machine determining a Doppler shift of each of the echoes; and
based at least on the Doppler shift determined for each of the echoes, the ultrasound machine generating a spectrogram of renal blood flow velocity versus time that includes the first velocity waveform of renal blood flow;
calculating a first power spectrum of first maximum blood flow velocity of the first velocity waveform of renal blood flow, the first power spectrum indicating a baseline stress level of the subject;
assessing a current stress level of the subject by:

receiving second data indicating a second velocity waveform of renal blood flow of the subject at a current time;

calculating a second power spectrum of second maximum blood flow velocity of the second velocity waveform of renal blood flow, the second power spectrum indicating the current stress level of the subject; and comparing the second power spectrum to the first power spectrum to determine a relative stress level of the subject corresponding to a difference between the current stress level and the baseline stress level; and in response to the relative stress level exceeding a predetermined threshold, recommending a stress-reduction treatment for the subject to reduce the relative stress level.

14. The processor of claim 13, wherein the first data comprises an image of the first velocity waveform of the renal blood flow, the operations further comprising deriving the first maximum blood flow velocity from the first data by extracting data points representing an envelope of the velocity waveform from the image, the extracted data points collectively forming the first maximum blood flow velocity.

15. The processor of claim 13, wherein the calculating comprises performing a Fast Fourier Transform (FFT) on the first maximum blood flow velocity to generate the first power spectrum of the first maximum blood flow velocity as a function of frequency.

16. The processor of claim 13, wherein the stress-reduction treatment comprises at least one of a medication, counseling, or meditation.

17. The processor of claim 13, the operations further comprising, in response to the relative stress level exceeding the predetermined threshold, recommending postponement of a medical procedure until a later time, wherein the stress-reduction treatment is recommended for the subject to reduce the relative stress level prior to the later time and to improve a likelihood of a successful outcome to the medical procedure.

18. The processor of claim 13, the operations further comprising:

receiving third data comprising measurements of a biological function of the subject, the third data being captured simultaneously with the first data;

calculating a stress level of the subject based on the third data using a stress algorithm of calculating stress based on measurements of the biological function; and tuning the stress algorithm so that the stress level calculated according to the stress algorithm corresponds to the stress level indicated by the first power spectrum.

19. An ultrasound machine comprising:

a sonography head configured to:
   emit sound waves into a subject that encounter blood that flows through a renal artery of the subject; and
   receive echoes of the emitted sound waves that result from at least partial reflection of the sound waves that encounter the blood that flows through the renal artery of the subject;

a base unit coupled to the sonography head, the base unit configured to:
   determine a Doppler shift of each of the echoes;
   based at least on the Doppler shift determined for each of the echoes, generate a spectrogram of renal blood flow velocity versus time that includes a velocity waveform of renal blood flow of the subject; and
   calculate a power spectrum of maximum blood flow velocity of the velocity waveform of renal blood flow, the power spectrum indicating a stress level of the subject; and a display device coupled to the base unit, the display device configured to:
   display images corresponding to the velocity waveform of renal blood flow of the subject; and
   display stress information of the subject, wherein the displayed stress information includes or is based on the power spectrum.

* * * * *